United States Patent [19]
Borror et al.

[11] Patent Number: 6,036,992
[45] Date of Patent: Mar. 14, 2000

[54] PROCESS OF MAKING AN ENTERAL FORMULA CONTAINING LONG-CHAIN POLYUNSATURATED FATTY ACIDS

[75] Inventors: David A. Borror, Westerville; David V. Diodato, Hilliard, both of Ohio; Debra L. Ponder, Morristown, N.J.; Margaret H. Dohnalek, Worthington, Ohio

[73] Assignee: Abbott Laboratories, Abbott Park, Ill.

[21] Appl. No.: 09/270,423

[22] Filed: Mar. 16, 1999

Related U.S. Application Data

[63] Continuation of application No. 08/825,314, Mar. 28, 1997, abandoned.

[51] Int. Cl.[7] ................................. A23J 7/00; A23L 1/10; A23L 1/32
[52] U.S. Cl. .................... 426/662; 426/801; 426/614; 514/580
[58] Field of Search ..................... 426/801, 662, 426/614; 514/580

[56] References Cited

U.S. PATENT DOCUMENTS 5,066,500  11/1991  Gil et al. .
5,589,357  12/1996  Martinez et al. .

*Primary Examiner*—Anthony J. Weier
*Attorney, Agent, or Firm*—Thomas D. Brainard

[57] ABSTRACT

Enteral formulas that contain long-chain polyunsaturated fatty acids (PUFAs) and a process for making such enteral compositions are described. More particularly, the invention relates to enteral compositions which provide long chain PUFAs arachidonic acid (AA) and docosahexaenoic acid (DHA) essentially free of cholesterol and may be derived from egg yolk lipids, and thus are predominantly in a phospholipid form. The process of making such a composition provides improved organoleptic and stability properties. Enteral compositions according to this invention may be used to feed infants, particularly pre-term infants, to promote neural development and development of visual acuity, and to reduce the incidence of necrotizing enterocolitis.

18 Claims, No Drawings

PROCESS OF MAKING AN ENTERAL FORMULA CONTAINING LONG-CHAIN POLYUNSATURATED FATTY ACIDS

This application is a continuation of application Ser. No. 08/825,314, filed Mar. 28, 1997, now abandoned.

TECHNICAL FIELD

The present invention relates generally to enteral formulas that contain long-chain polyunsaturated fatty acids (PUFAs) and to a process for making such enteral compositions. More particularly, the present invention relates to enteral compositions which provide long chain PUFAs arachidonic acid (AA) and docosahexaenoic acid (DHA) essentially free of cholesterol and may be derived from egg yolk lipids. Long chain PUFAs provided from egg yolk are predominantly in a phospholipid form. The process of making such asDcomposition provides improved organoleptic and stability properties.

BACKGROUND OF THE INVENTION

Long chain PUFAs in enteral formulas or compositions have been the subject of diverse literature. For example, U.S. Pat. No. 4,670,285 ("Clandinin") discloses a specific fat blend suitable for use in infants formulas. More specifically, the Clandinin fat blend contains at least one $C_{20}$ or $C_{22}$ ω-6 fatty acid and a $C_{20}$ or $C_{22}$ ω-3 fatty acid. These fatty acids are disclosed as being at certain, defined amounts to avoid causing harmful effects to an infant fed the fat blend. The $C_{20}$ or $C_{22}$ ω-6fatty acids are present in a total amount of about 0.13 to 5.6% by weight of all fatty acids in the product. The $C_{20}$ or $C_{22}$ ω-3 fatty acid, if present, are included in a total amount of about 0.013 to 3.33% by weight of all fatty acids in the product. Clandinin discloses the use of egg lipids to supply the ω-6 and ω-3 fatty acids; however, the egg lipid used by Clandinin also contains high levels of cholesterol. Further, this reference teaches the use of 75 to 95 parts by wt. of egg yolk lipid with the remainder of the oil being coconut oil or soybean oil. The nomenclature used by Clandinin for fatty acids will be utilized herein.

WO 93/20717 discloses an infant formula which contains no more than sub-irritant amounts of free long chain ($C_{16}$–$C_{22}$) fatty acids and triglycerides. This application also discloses that providing lower alkyl esters, such as ethyl esters, of such fatty acids in infant formula essentially eliminates the tendency of the free fatty acid to damage the intestinal epithelium of the infant, but permits absorption and processing of the fatty acid moiety.

U.S. Pat. No. 4,918,063 to Lichtenberger discloses compositions containing unique-mixtures of phospholipids and neutral lipids for the prevention or treatment of ulcers and inflammatory bowel disease. This patent discloses mixtures of saturated or unsaturated phospholipids, together with saturated or unsaturated triglycerides and/or sterols, as providing ulcer protective efficacy in experimental animal models. This patent also teaches the inclusion of polyvalent cations or antioxidants to the lipid mixture to enhance activity.

International Publication No. WO 96/10922 to Kohn et al. discloses a fat mixture for infant formula characterized in that arachidonic acid and docosahexaenoic acid are present in the fat mixture in the form of phospholipids.

European Patent Application 0 376 628 B1 to Tomarelli discloses an all vegetable oil fat composition which utilizes randorsmized palm oil or randomized palm olein oil as the sole palmitic acid oil source. It is also disclosed that the all vegetable oil fat compositions are particularly suited for use in infant formulas for pre-term (or low birth weight) infants. The pre-term fat compositions of the Tomarelli application include medium chain triglycerides (MCT's) with a randomized palmitic acid oil, lauric acid oil, an oleic acid oil and a linoleic acid oil.

Although the references discussed above have made important contributions, there remains a need for infant formulas that contain egg phospholipids as a source of long chain PUFAs in concentrations appropriate for nutrition. A further need remains for methods of preparing enteral formulas containing egg phospholipids such that the formulas have acceptable organoleptic properties. Such compositions have particular application in infant formula for term and/or preterm infants, whose needs for long chain PUFAs are established for the proper neural development and for development of visual acuity. In addition, there may be a protective effect on the gut.

Necrotizing enterocolitis (NEC) is a serious problem in infants having birth weights of less than about 1500 grams. Despite almost three (3) decades of study, the precise etiology and pathophysiology of NEC remains unclear. NEC is a life-threatening disease characterized by ischemic necrosis of the involved alimentary tract structures and pneumatosis intestinalis, which often results in the perforation of the bowel. A pre-term infant with NEC presents a clinical picture of thermal instability, lethargy, gastric retention, vomiting, abdominal distension, gross or occult blood in the stools and radiographic evidence of pneumatosis intestinalis, air in the portal veins or pneumoperitoneum. Apnea spells, shock and sclerema rapidly appear and death is common.

Numerous authors have made varied observations and posited factors influence this malady. (Nue, *Pediatr. Clin. North. Am.*, April, 1996, 43(2): 409–32). The following observations and factors are exemplary:

Flageole et al., Necrotizing Enterocolitis of the Newborn, Review for the Clinician. Union-Med-Can. 1991 September-October; 120(5): 334–8, suggest the pathogenesis of NEC includes mesenteric ischemia, gastrointestinal immaturity, enteral feedings and even possibly infection;

Caplan et al., Role of Platelet Activating Factor and Tumor Necrosis Factor-Alpha in Neonatal Necrotizing Enterocolitis, *Journal of Pediatrics*, Jun., 1990, 960–964, report platelet activating factor and tumor necrosis factor-alpha are elevated in patients with NEC;

Kliegman et al., Clostridia as Pathogens in Neonatal Necrotizing Enterocolitis, *The Journal of Pediatrics*, August, 1979, 287–289, reports the isolation of *Clostridia perfringens* from children with neonatal NEC;

Ostertag et al., Early Enteral Feeding Does Not Affect the Incidence of Necrotizing Enterocolitis, *Pediatrics*, Vol. 77, No. 3, March 1986, 275–280, reports that dilute, early enteral calories do not adversely affect the incidence of NEC;

Bell et al., Neonatal Necrotizing Enterocolitis, *Annals of Surgery*, Vol. 187, January 1978, No. 1, 1–7, suggests the use of combination antimicrobial therapy for the treatment of infants with NEC;

Eyal et al., Necrotizing Enterocolitis in the Very Low Birth Weight Infant: Expressed Breast Milk Feeding Compared with Parenteral Feeding, *Archives of Disease in Childhood*, 1982, 57, 274–276 reports that the incidence of NEC in low birth weight infants was reduced by delaying the initiation of enteral feeding.

Finer et al., Vitamin E and Necrotizing Enterocolitis, *Pediatrics*, Vol. 73, No. 3, March 1984 suggests that administration of vitamin E to reduce the incidence of severe sequelae from retrolental fibroplasia may be associated with an increased incidence of NEC.

Brown et al., Preventing Necrotizing Enterocolitis in Neonates, *JAMA*, Nov. 24, 1978, Vol. 240, No. 22, 2452–2454 reports that NEC can be virtually eliminated by the use of a slowly progressive feeding regimen.

Kosloske, Pathogenesis and Prevention of Necrotizing Enterocolitis: A Hypothesis Based on Personal Observation and a Review of the Literature, *Pediatrics*, Vol. 74, No. 6, December 1984, 1086–1092, hypothesizes that NEC occurs by the coincidence of two of three pathological events: (1) intestinal ischemia; (2) colonization by pathogenic bacteria; and (3) excess protein substrate in the intestinal lumen.

Kosloske, supra, also reports that NEC is rare among infants fed only breast milk. In humans, breast milk plays a role in passive immunization of the neonatal intestine, and contains factors that promote the growth of Bifidobacterium in the intestinal flora. It is also reported that the beneficial contents of human milk may be adversely affected by freezing, pasteurization, or storage.

Thus, there is much debate about the etiology and treatment of NEC and there remains a need for compositions and methods that are better able to cure and/or reduce the incidence of this devastating and frequently fatal condition.

SUMMARY OF THE INVENTION

The present invention has many aspects. In a first aspect, the invention provides a process for the production of an enteral formula comprising egg yolk phospholipids, said method comprising the steps of:

(a) providing dried egg phosphatide powder essentially free of cholesterol;

(b) dispersing said phospholipid fraction in an aqueous phase to form a phospholipid dispersion; and (c) combining said phospholipid dispersion with slurries of other components of said enteral formula.

The invention further provides for the production of an infant formula containing egg phospholipids having improved organoleptic properties comprising the steps of:

(a) forming a 2–15% by weight aqueous dispersion of egg phospholipids;

(b) subjecting said dispersion to de-aeration;

(c) combining said de-aerated dispersion with a mixture of protein, carbohydrates, vitamins and minerals to form said infant formula; and (d) homogenizing said infant formula.

Preferably, the aqueous dispersions provide egg phosphatide at about 2 to about 15 percent by weight, more preferably about 6 to about 10 percent; and are in water at about 20 to 50° C., more preferably about ambient temperature, or 25° C.

In another aspect, the invention provides improved enteral formulas containing arachidonic acid and docosahexaenoic acid, characterized in that said arachidonic and docosahexaenoic acid are in the form of phospholipids, said enteral formula produced by a process comprising the steps of:

(a) forming a 2–15% by weight aqueous dispersion of said phospholipid;

(b) subjecting said dispersion to de-aeration;

(c) combining said de-aerated dispersion with at least one member selected from the group of protein, carbohydrate, vitamins and minerals to form said enteral formula; and (d) homogenizing said enteral formula.

In another aspect, the invention provides a method for increasing the levels of arachidonic acid and docosahexaenoic acid in human blood serum, said method comprising the step of administering to said human the enteral formula described herein.

In yet another aspect, the invention provides a formula suitable for feeding infants,-the formula comprising protein, carbohydrates and lipids, the improvement characterized in a lipid blend comprising medium chain triglycerides and egg phospholipid, wherein said egg phospholipid is present at a level from about 1 wt. % to about 40 wt. %, preferably from 5 to 30 wt. %, of the lipid blend and wherein said egg phospholipid is essentially free of cholesterol.

Preferably, this improved formula further comprises arachidonic acid in a concentration of from about 80 to about 250 mg per liter or from about 10 to about 31 mg per 100 kcals; and optionally further comprises docosahexaenoic acid in a concentration of from about 25 to about 130 mg per liter or about 3 to about 16 mg per 100 kcals such that the ratio of arachidonic acid to docosahexaenoic acid ranges from about 4:1 to about 2:1. Put another way, the improved formula further comprises total long chain ω-6 fatty acids in a concentration of from about 100 to about 425 mg per liter or about 12 to about 53 mg per 100 kcals; and further optionally comprises total long chain ω-3 fatty acids in a concentration of from about 40 to about 185 mg per liter or about 5 to about 23 mg per 100 kcals, such that the ratio of long chain ω-6 fatty acids to long chain ω-3 fatty acids ranges from about 2:1 to about 3:1, preferably about 2.5:1.

Expressed differently, the improved formula further comprises arachidonic acid and/or total long chain ω-6 fatty acids in a weight ratio as a percent of total lipid blend of from about 0.2 to about 0.6 percent, preferably about 0.4 percent. The formula may optionally also comprise docosahexaenoic acid and/or total long chain ω-3 fatty acids in a weight ratio as a percent of total lipid blend of from about 0.06 to about 0.3 percent, preferably about 0.12 percent.

Other aspects of the invention are described throughout the application.

DETAILED DESCRIPTION OF THE INVENTION

General Terminology

Fatty acids are hydrocarbon chains of various lengths, having a carboxylic acid at one end, thus making them somewhat polar and hydrophilic at this location, while being otherwise hydrophobic to varying degrees depending on the length of the hydrocarbon chain. Fatty acids are categorized by the length of the hydrocarbon chain. For example, chains of fewer than about 6 carbons are considered "short"; chains of about 6–18 carbons are "medium" and chains of 20 or more carbons are considered "long". Fatty acids may also have one or more double bonds which are points of "unsaturation" in the hydrocarbon chain. As used herein, the term "long chain PUFA" means a fatty acid of twenty carbon atoms or more having at least two carbon-carbon double bonds (polyunsaturated). The number and position of double bonds in fatty acids are designated by a convention of nomenclature. For example, arachidonic acid ("AA" or "ARA") has a chain length of 20 carbons and 4 double bonds beginning at the sixth carbon from the methyl end. As a result, it is referred to as "$C_{20}$:4 ω-6". Similarly, docosahexaenoic acid ("DHA") has a chain length of 22 carbons with 6 double bonds beginning with the third carbon from the methyl end and is designated "$C_{22}{:}6\ \omega\text{-}3$". Less prevalent long chain PUFAs are also known and some are listed in Tables I and IV (below the solid line divider).

"Glycerides" are complex lipids having a glycerol backbone esterified to fatty acids. A "triglyceride" (i.e. "triacylglycerol") has three esterified fatty acids, one to each hydroxyl site on the glycerol backbone. Di- and mono-glycerides have, respectively, two and one esterified fatty acid. A phosphoglyceride (i.e. "phospholipids" or "phosphatides"—all used interchangeably) differs from a triglyceride in having a maximum of two esterified fatty acids, while the third position of the glycerol backbone is esterified to phosphoric acid, becoming a "phosphatidic acid". In nature, phosphatidic acid is usually associated with an alcohol which contributes a strongly polar "head". Two such alcohols commonly found in nature are choline and enthanolamine. A "lecithin" is a phosphatidic acid associated with the aminoalcohol, "choline", and is also known as "phosphatidylcholine". Lecithins vary in the content of the fatty acid component and can be sources from, for example, eggs and soy. Cephalin (phosphatidylethanolamine), phosphatidylserine and phosphatidylinositol are other phosphoglycerides.

Phospholipids are commonly found in the membranes of all living systems. Traditional sources of phospholipids are egg yolk and soya bean oil. Phospholipids may also be obtained from mammalian brain, kidney, heart and lung; or from milk fat globule membranes. In addition, sources of microbial origin (single cell oils) such as algal and fungal oils may be used, particularly for the AA and DHA fatty acid components of phospholipids.

Hens' eggs are a relatively abundant source of lipids. Approximately 33% of the yolk of a hen's egg is lipid, of which about 67% is triglyceride, 28% is phospholipid, and the remainder is mostly cholesterol (percentages are by weight). These figures are approximate and will vary to some degree, depending on the diet, breed and conditions of the hens.

Compositions

Compositions useful in the invention comprise $\omega\text{-}6$ and/or $\omega\text{-}3$ long chain PUFAs. The source of the long chain PUFA is not critical. Known sources of long chain PUFA include fish or marine oil, egg yolk lipid and phospholipids, single cell oils (e.g., algal oils and fungal oils), it being understood in the art that some sources are better than others for achieving higher amounts of specific long chain PUFAs. Other edible, semi-purified or purified sources of long chain PUFAs will be evident to persons skilled in the art. New sources of long chain PUFAs may be developed through the genetic manipulation of vegetables and oil-bearing plants, and the use of such recombinant products is also contemplated in the present invention.

The long chain PUFA may be provided in the composition in the form of esters of free fatty acids; mono-, di- and tri-glycerides; phosphoglycerides, including lecithins; and/or mixtures thereof. A presently preferred source, at least when processed such that the organoleptic properties and cholesterol level are acceptable, appears to be egg yolk phospholipids.

The $\omega\text{-}6$ and/or $\omega\text{-}3$ fatty long chain PUFA may be administered in the form of an intravenous (i.e. parenteral) solution. An intravenous solution will preferably contain from 20 to 200 mgs of $\omega\text{-}6$ long chain PUFA per liter of intravenous solution and 10 to 50 mgs of $\omega\text{-}3$ long chain PUFA per liter of intravenous solution. Parenteral compositions will generally include suitable vehicles and excipients, such as buffers, preservatives, and the like.

The $\omega\text{-}6$ and/or $\omega\text{-}3$ fatty long chain PUFA may alternatively be administered in the form of an enteral composition. Enteral compositions containing the long chain PUFA may be in the form of a solution or an emulsion of active ingredient; or in a nutritional matrix comprising protein, carbohydrates, other fats, minerals and vitamins. Enteral compositions containing long chain PUFAs may provide either supplemental or complete nutritional support. The concentration of the long chain PUFA in the enteral composition can range from almost 100% by weight (as in the case of a bolus emulsion) to 0.5% by weight (as in the case of a nutritionally complete formula) of the composition depending on the mode of administration and intended purpose. In complete nutritional formulas the concentration may be even lower if enough of the formula is administered to deliver effective amounts of the long chain PUFA.

A particularly preferred embodiment of this invention relates to an improved, nutritionally complete formula suitable for feeding to infants, including pre-term infants. Such a preferred composition comprises protein, carbohydrates and lipids, wherein from about 6 to about 40 wt. % of the total lipid is egg phospholipid which is essentially free of cholesterol. The term "essentially free" means that the cholesterol content of the egg phospholipid is less than 0.1 wt. % and preferablyless than 0.05 wt. % of total lipid.

Those skilled in the art will readily understand what is meant by an infant formula. A typical infant formula contains about 10–35 gms of protein per liter of formula; 20–50 gms of lipid per liter of formula; 60–110 gms of carbohydrates per liter of formula and other various components such as vitamins, minerals, fibers, emulsifiers and the like. For purposes of understanding the components of an infant formula and methods for its production, the following U.S. patents are herein incorporated by reference: 1) U.S. Pat. No. 5,492,899 to Masor et al.; 2) U.S. Pat. No. 5,021,245 to Borschel et al.; 3) U.S. Pat. No. 5,234,702 to Katz et al.; and 4) U.S. Pat. No. 5,602,109 to Masor et al.; and 5) U.S. Pat. No. 4,670,268 to Mahmoud. More specifically, this embodiment of the invention comprehends an infant formula containing about 40–50 gms of lipid per liter of formula wherein the lipid comprises a blend of medium chain triglycerides and egg phospholipid that is essentially free of cholesterol. Typically, the lipid blend comprises from about 1–40 wt. %, more preferably about 5 to about 30 wt. %, of the egg phospholipid. This embodiment is specifically designed to provide long chain PUFAs selected from $\omega\text{-}3$ fatty acids and $\omega\text{-}6$ fatty acids in amounts beneficial to infants.

Process of making

Since hens' egg yolks include both triglycerides and phosphatides, it may be preferable to process the egg yolks using organic solvents in a manner that separates the phosphatides from triglycerides, sterols (e.g. cholesterol) and other components. Various literature methods are suitable for this separation, at least in laboratory scale. Altematively, such egg phosphatides essentially free of cholesterol are commercially available in dried powder form from Pfanstiehl, Inc. (Waukegan, Ill.) as Catalog No. P-123.

The egg phosphatide is then incorporated into the enteral composition of the present invention. Because of the lipid content, incorporation of the egg phosphatides into an enteral formula was expected to be facile in an oil phase. However, it was surprisingly discovered that these lipid-lipid dispersions were unacceptable and that preparation of an aqueous dispersion of the egg phosphatide resulted in improved product. Aqueous dispersions of about 2–15 wt %, preferably about 3 to about 8 wt %, should be made in cool to ambient water (about 20–25° C.) to provide the best results. Warmer water produced less acceptable organoleptic properties.

Separately, the carbohydrate, protein and lipid slurries that comprise the macronutrient source are prepared as is known in the art, and these slurries are mixed at about 130 to 140° C. Just prior to homogenization, the phosphatide dispersion is mixed with the remainder of the formula.

In a particularly preferred variation, prior to the addition of the phosphatide dispersion to the final product mix (just before homogenization) the phosphatide dispersion is de-aerated under a moderate vacuum. De-aeration may be effected by any mechanism but an atomizing de-aerator at about 15 inches Hg provided satisfactory results. This additional step has been shown to improve the organoleptic and olfactory properties of the final product, even more so than activated carbon filtration or a combination of the two (see Example III).

For making parenteral compositions useful in this invention, conventional sterile parenteral production technology may be used. It may be preferable in this case to avoid the egg phosphatides and employ instead the triglyceride oils or fatty acid esters, such as may be found in recombinant or single cell oil sources.

Utility

Compositions of the present invention are useful in the nutritional support of infants. The addition of long chain PUFAs, especially ω-6 and ω-3 fatty acids and most especially AA and DHA have generally been considered to be beneficial to neural development and visual acuity of the infant, although conflicting reports have also been found in the literature.

Compositions of the present invention, containing long chain PUFAs selected from ω-6 and ω-3 fatty acids, have surprisingly also been found useful to reduce substantially the incidence of NEC in infant populations that are susceptible to NEC. In a more specific embodiment, the method of reducing the incidence of NEC is accomplished through the administration of arachidonic acid (AA, 20:4 ω-6) or, more preferably, AA in combination with docosahexaenoic acid (DHA, 22:6 ω-3).

More broadly, this aspect of the invention contemplates a method for reducing the incidence of necrotizing enterocolitis in an infant which is susceptible to necrotizing enterocolitis, said method comprising the administration of an effective amount of at least one long chain PUFA selected from the group of $C_{20}$ω-6 fatty acids, $C_{22}$ω-6 fatty acids, $C_{20}$ω-3 fatty acids and $C_{22}$ω-3 fatty acids. The administration is at a level of at least 1.0 mg of ω-3 fatty acids per kilogram of infant weight per day. A more preferred embodiment uses a combination of ω-6 and ω-3 fatty acids at weight ratios of about 2:1 to about 4:1.

There is further disclosed a method for dedreasing the occurrence of necrotizing enterocolitis in a human infant, said method comprising administering to the infant egg phospholipids in an amount to result in at least 1.0 mgs of long chain ω-6 fatty acids per day. Preferably the egg phospholipids supplies AA as a significant portion of the ω-6 fatty acids and preferably also supplies DHA and/or other long chain ω-3 fatty acids in the ratios mentioned above.

An additional aspect of this invention relates to the enteral administration to humans of phospholipids of AA and DHA which readily increase the blood serum levels of fatty acids sPA and DHA in humans relative to compositions having triglycerides of AA and DHA.

A more appropriate measure of long chain PUFA administration is in mgs of AA and DHA per day. In a preferred embodiment, at least 1.0 mgs of AA and/or at least 0.5 mgs of DHA should be administered to the infant per day. More preferably, the minimum dosage is 4.0 mgs of AA and 1.0 mgs of DHA per day. From another vantage point, the method of this invention can be accomplished through the administration of from 1.0 mg to 4.0 mg of AA per kilogram (of the infant) per day and from 0.25 to 1.0 mg of DHA per kilogram per day. In a more preferred embodiment, the AA and DHA are administered in the form of a phospholipid or phosphatide.

The AA and/or DHA can be administered individually, as separate components, or together, or in combination with other ingredients such as protein, lipid, carbohydrate, vitamins and minerals. Nutritional support for low birth weight infants is either parenteral (intravenous feeding) or enteral. Thus, the appropriate levels of long chain PUFA can be incorporated into the parenteral nutrition solution or added to a conventional low birth weight enteral formula. Most preferably, the method of the present invention is accomplished through the enteral administration of an infant formula designed for low-birth weight infants containing AA and DHA. Such an infant formula further comprises appropriate levels of carbohydrate and protein and an appropriate combination of minerals and vitamins. An exemplary infant formula for use in the methods of the present invention is a modified Similac Special Care® (Ross Products Division of Abbott Laboratories, Columbus, Ohio), which is discussed in more detail in Example II.

An additional aspect of this invention is a method for increasing the blood serum levels of arachidonic acid and docosahexaenoic acid in human blood serum, said method comprising the step of administering to said human an enteral formula containing AA and DHA in the form of phospholipids.

Recent studies by the present Applicants have indicated that the administration of long chain PUFA to infants susceptible to NEC will reduce the incidence of NEC and may also reduce the level or severity of NEC. The Applicants have also discovered that the administration of phospholipids from animal or vegetable sources is also effective in reducing the incidence of NEC in infant populations that are susceptible to NEC.

EXAMPLE I

Egg yolk phosphatide was obtained from Pfanstiehl, Inc. (Waukegan, Ill. - Catalog No. P-123) and was used in the following Examples. The fatty acid and cholesterol profile of this egg phosphatide is set forth in Table I. The sum of all ω-3 and of all ω-6 "long chains" PUFAs is also given.

TABLE I

Fatty Acid Profile and Cholesterol Content of Egg Yolk Lecithin

| Fatty Acid | gm/100 gm of sample | |
|---|---|---|
| C14:0 | 0.08 | |
| C16:0 | 18.83 | |
| C16:1 ω-7 | 0.82 | |
| C16:4 | 0.21 | |
| C18:0 | 6.72 | |
| C18:1 ω-9 | 17.36 | |
| C18:2 ω-6 | 9.8 | |
| C20:1 ω-9 | 0.11 | |
| C20:2 ω-6 | | 0.24 |
| C20:3 ω-6 | | 0.3 |
| C20:4 ω-6 - arachidonic | | 4.93 |
| C22:0 | 0.07 | |
| C22:4 ω-6 | | 0.3 |
| C22:5 ω-6 | | 1.45 |
| C22:5 ω-3 | 0.09 | |

TABLE I-continued

Fatty Acid Profile and Cholesterol Content of Egg Yolk Lecithin

| Fatty Acid | gm/100 gm of sample | |
|---|---|---|
| C22:6 ω-3 - docosahexaenoic | 1.24 | |
| cholesterol | | <0.05 |
| Total LCPUFA ω-6 | | 7.22 |
| Total LCPUFA ω-3 | 1.33 | |

Those skilled in the art will appreciate that the specific levels of the various fatty acids contained in egg yolk lipid will vary depending on the breed, diet and age of the hen. In addition, the extraction procedure used by Pfanstiehl to prepare the phosphatide used in the Examples results in a material that contains extremely low levels of cholesterol while possessing a fatty acid profile that is highly useful in the nutritional arts.

EXAMPLE II

In this example, "Experimental" and "Control" infant formulas were prepared, respectively, with and without the egg phosphatide of Example I. Tne Control composition was Similac Special Care® (Ross Products Division of Abbott Laboratories, Columbus, Ohio) and was prepared using the following list of ingredients, which results in the formula having the composition set forth in Tables II–IV, below:

Water (Kosher), nonfat milk, hydrolyzed cornstarch, lactose, fractionated coconut oil (medium-chain triglycerides), whey protein concentrate, soy oil, coconut oil, calcium phosphate tribasic, potassium citrate, sodium citrate, magnesium chloride, ascorbic acid, mono- and diglycerides, soy lecithin, calcium carbonate, carrageenan, choline chloride, ferrous sulfate, m-inositol, taurine, niacinamide, L-camitine, alpha-tocopherol acetate, zinc sulfate, calcium pantothenate, potassium chloride, cupric sulfate, riboflavin and vitamin A palmitate, thiamin chloride hydrochloride, pyridoxine hydrochloride, biotin, folic acid, manganese sulfate, phylloquinone, vitamin $D_3$, sodium selenite and cyanocobalamin.

Generally, protein, carbohydrate, lipid, vitamin and mineral slurries are separately prepared and then these are mixed prior to homogenization as is generally taught in the previously incorporated U.S. patents relating to the manufacture of infant formula.

In the experimental formula, the egg phosphatide of Example I was incorporated into the formula during manufacture. First, the egg phosphatide was dispersed in water at 25° C. to make an 8% dispersion. Just prior to homogenization the phosphatide dispersion was combined with the protein, carbohydrate, vitamin, mineral and other lipid slurries to result in an "Experimentals" formula havisbg the composition shown in Tables II–IV, below. The amounts of each component are given both on a "per Liters" basis and on a "per kcals" basis since it is well known in the art to prepare infant formulas having higher or lower caloric densities than the standard 20 kcal per fluid ounce.

TABLE II

COMPONENTS of CONTROL AND EXPERIMENTAL FORMULAS

| | Preferred Ranges | |
|---|---|---|
| Nutrient | Units Per Liter* | Units per 100 kcal |
| Protein, g | 21.9–23.4 | 2.61–2.88 |
| Fat, g (as described in Table III below) | 44.0–46.0 | 5.24–5.67 |
| Carbohydrate, g | 84.0–88.0 | 10.00–10.84 |
| [Ash, g] | 6.7–8.0 | 0.80–0.99 |
| Total Solids, g | 158.6–165.0 | 18.88–20.32 |
| Linoleic Acid, g | 5.6–12.2 | 0.67–1.50 |
| Calcium, mg | 1300–1700 | 154.76–209.36 |
| Phosphorus, mg | 720–970 | 85.71–119.46 |
| Magnesium, rng | 100–170 | 11.90–20.94 |
| Sodium, mg | 349–389 | 41.55–47.91 |
| Potassium, mg | 1000–1420 | 119.05–174.88 |
| Chloride, mg | 650–770 | 77.38–94.83 |
| Iron, mg | 3.0–5.5 | 0.36–0.68 |
| Zinc, mg | 12.0–14.6 | 1.43–1.80 |
| Copper, mg | 2.0–3.0 | 0.24–0.37 |
| Manganese, mcg | 100–500 | 11.90–61.58 |
| Iodine, mg | 0.05–0.30 | 0.01–0.04 |
| Selenium, mcg | 12–29 | 1.43–3.57 |
| Vitamin A, IU | 6000–8000 | 714.29–985.22 |
| Vitamin D, IU | 1200–1580 | 142.86–194.58 |
| Vitamin E, IU | 35.0–45 | 4.17–5.54 |
| Vitamin $K_1$, mcg | 100–140 | 11.90–17.24 |
| Vitamin C, mg | 350–450 | 41.67–55.42 |
| Thiamin ($B_1$), mg | 2.66–4.6 | 0.32–0.57 |
| Riboflavin ($B_2$), mg | 5.03–9.0 | 0.60–1.11 |
| Pyridoxine ($B_6$), mg | 2.6–3.4 | 0.31–0.42 |
| Vitamin $B_{12}$, mcg | 4.47–9.5 | 0.53–1.17 |
| Pantothenic Acid, mg | 15.4–24.0 | 1.83–2.96 |
| Folic Acid, mcg | 340–450 | 40.48–55.42 |
| Niacin, mg | 40.6–65 | 4.83–8.00 |
| Biotin, mcg | 350–460 | 41.67–56.65 |
| Choline, mg | 81–243 | 9.64–29.93 |
| m-Inositol, mg | 44.7–61 | 5.32–7.51 |
| L-Carnitine, mg | 35–60 | 4.17–7.39 |
| Taurine, mg | 60–80 | 7.14–9.85 |
| Energy (kcal) | 812–840 | |

*assumes 24 kcal per fluid oz.

The following Table III sets forth the lipid content (the only variable) used in the Control and Experimental products. It can be seen that the two formulas have the same total lipid amount, but differ principally in the exchange of egg phospholipid for a portion of the medium chain triglycerides.

TABLE III

Lipids for Control and Experimental Formulas

| Ingredient Lipid Blend | Control wt % | Experimental wt % |
|---|---|---|
| MCT* | 50 | 41 |
| coconut oil** | 30 | 30 |
| soy oil | 20 | 20 |
| egg phospholipid | 0 | 9 (4.0 gm/L) |
| soy lecithin | 0.45 gm/L | 0.45 gm/L |
| Cholesterol | ND+ | ND+ |
| Total Lipid (g/L) | 44.1 | 44.1 |

*MCT = medium chain triglycerides
**fractionated
+ND = none detected

Table IV sets forth the composite fatty acid profile for the Control and Experimental formulas. This represents the sum of the fatty acid components of the egg lecithin and the Similac Special Care® formula.

TABLE IV

Average Fatty Acid Profiles in Weight %

| Fatty Acid | Control | Experimental | |
|---|---|---|---|
| 6:0 - caproic | 0.71 | 0.27 | |
| 8:0 - caprylic | 30.56 | 23.11 | |
| 10:0 - capric | 19.61 | 16.44 | |
| 12:0 - lauric | 9.69 | 10.24 | |
| 14:0 - myristic | 3.85 | 4.08 | |
| 15:0 and 14:1 | 0.04 | 0.01 | |
| 16:0 - palmitoleic | 5.51 | 7.65 | |
| 16:1 - palmitoleic | 0.03 | 0.12 | |
| 16:2 | — | — | |
| 17:0 - margaric | 0.04 | 0.09 | |
| 16:3 | — | — | |
| 16:4 | — | — | |
| 18:0 - stearic | 2.68 | 3.89 | |
| 18:1 ω-9 - oleic | 8.31 | 11.25 | |
| 18:2 ω-6 - linoleic | 16.36 | 18.87 | |
| 18:3 ω-6 - linolenic | 2.3 | — | |
| 18:3 ω-3 | 2.24 | 2.45 | |
| 18:4 ω-6 | — | 0.02 | |
| 20:0 - arachidic | 0.12 | 0.14 | |
| 20:1 ω-9 | 0.04 | 0.09 | |
| 20:2 ω-9 | 0.02 | 0.02 | |
| 20:3 ω-9 | — | 0.05 | |
| 20:4 ω-6 - AA | — | — | 0.41 |
| 20:4 ω-3 | — | — | |
| 20:5 ω-3 | — | — | |
| 22:0 - behenic | 0.07 | 0.12 | |
| 22:5 ω-6 | — | — | 0.07 |
| 22:5 ω-3 | — | 0.07 | |
| 22:6 ω-3 - DHA | — | 0.14 | |
| 24:0 | 0.04 | 0.07 | |
| Total LC PUFA ω-3 | 0 | 0.21 | |
| Total LC PUFA ω-6 | | 0 | 0.48 |

The inclusion of the egg phosphatide resulted in 0.21 weight percent of the total lipid blend as long chains ω-3 fatty acids and 0.48 weight percent of the total lipid blend as long chain ω-6 fatty acids. More specifically, 0.14 weight percent of the total fat blend was DHA and 0.41 weight percent of the total lipid blend was AA. Based on administration of 100 kcal/kg/day for a 1 kg infant, this formula provides about 22 mg of AA and about 7 mg of DHA per day.

EXAMPLE III

In this experiment, process variables were evaluated in an effort to reduce the organoleptic drawbacks associated with the use of egg phospholipids. The isolation of egg phospholipids useful in the present invention often results in an egg phosphatide that has somewhat objectionable organoleptic properties for use in an infant formula. These can be improved yet further to provide a product that is not objectionable to either the infant or the care giver. This process to improve the final product is described below.

A number of nutritional formulas similar to Example II were prepared except that 6% by wt. of the fat blend was egg phospholipid which was pre-treated using various procedures. Egg phospholipid was dispersed in a portion of the oil blend described in Example II or in a portion of the water. The oil dispersions were unacceptable and could not be used even after heating to about 95° C. The dispersion of the phospholipid into water from ambient to warm temperature was accomplished easily and is the preferred means of forming the water dispersion.

A master batch of 3% by wt. egg phospholipid dispersion was prepared by blending the phospholipid in 90° C. water for about 1 hour. A portion of this dispersion was passed through: (1) a de-aerator alone; (2) a carbon filtration unit alone; (3) a de-aerator and a carbon filtration unit combined; or (4) no treatment.

The activated carbon filtration unit contained 80 gms of activated carbon and the de-aeration unit was operated at a moderate vacuum (15 in. Hg). The batch portions were passed through the filtration unit 3 times and through the de-aerator once. When both techniques were used, the portion was passed through the filter first, then the de-aerator. The treated portions were then added to respective nutritional formulas just prior to homogenization and sample packaging.

The samples were then initially evaluated for "flavor notes" (organoleptic properties) by a panel of trained evaluators. The results of the panel are set forth in Table V.

TABLE V

Infant Formula with Egg Yolk Phospholipids
Organoleptic Quality Results

| | Flavor Notes* | | | |
|---|---|---|---|---|
| Treatment of Dispersion | Initial | AA | AAL at 3 months | |
| De-aeration alone | AA | 1–2.5 | AAL | 2.5 |
| Carbon Filtration alone | AA | 1.5–2 | AAL | 2.5 |
| De-aeration/Carbon Filtration | AA | 2 | AAL | 2.5 |
| No Treatment | AA | 2.5–3 | AAL | 3 |

*Flavor Notes
AA = Arachidonic Acid
AAL = Arachidonic Acid Lingering
+Scale
0.5 Very slight; 1 Slight, 1.5 Slight to Moderate; 2 Moderate; 2.5 Moderate to Strong; and 3 Strong Surprisingly, the least aromatic sample was that which contained the dispersion that was passed through the de-aerator only. The dispersion that was passed through the de-aerator and the carbon filter had the poorest rating except for the control (no treatment of phospholipid dispersion).

EXAMPLE IV

Formulas prepared in accordance with Examples II and III were fed to infants in a study conducted in the Neonatal Nursery of the University of Tennessee Newborn Center under the direction of Dr. Susan E. Carlson with financial support from Ross Products Division of Abbott Laboratories (Study AE78), NICHD grant RO1-HD31329, and National Eye Institute grant RO1-EY08770. Research parameters included growth, neuro development, and visual acuity. Long chain PUFAs are believed to be physiologically important for the development of the brain and eye, and are rapidly accumulated in fetal tissues in the last trimester of pregnancy. Thus, pre-term infants do not accrete normal levels of long chain PUFAs relative to term infants.

Inclusion criteria: Entry into this clinical study was based on a "low" birth weight of less than 1500 gm (range 750–1375 gm) with no evidence of cardiac, respiratory, gastrointestinal or other systemic disease. The infant also had no history of birth asphyxia or clinical complications of blood group incompatibility. The mothers of the enrolled infants had no medical history of prenatal infections with proven adverse effects on the fetus. Maternal substance abuse was an exclusion criteria. All infants initiated oral feedings by day 7 of life.

During the clinical study, a total of 119 infants were enrolled within the first 7 days of life. With the exception of one infant who was transferred to another hospital shortly after enrollment (Control), all other infants (n-118) were cared for in the same hospital. Infants were enrolled (randomized, blind) into 1 of 3 groups, two of which received the Control formula during their hospitalization and one of which received the Experimental formula (see Example II). Infants lost during hospitalization were replaced by another infant assigned to the same treatment group. Because of the study design, more infants were fed the Control formula. The total number fed the Control formula was more than twice the number fed the Experimental formula. 85 infants completed the in-hospital phase of the study.

Findings: A surprising finding was that there appeared to be a higher incidence of necrotizing enterocolitis (NEC) in one of the randomized groups. The blind was broken early to determine if the Experimental Formula was causing this high incidence. Surprisingly, the Control Groups were experiencing a higher incidence of NEC than the Experimental Group.

Table VI groups the total number of neonates according to treatment (Control v. Experimental) and sets forth the number of neonates in each group that developed NEC. NEC was considered present or suspect when clinical signs and symptoms consistent with this disease, such as abdominal distention, gastric residuals, bilious vomiting, heme positive stools, presence of mucosa in stools, and presence of C-reactive protein at $\geq 0.5$ mg/dL (Pourcyrous et al., "Significance of Serial C-reactive Protein Responses in Neonatal Infection and Other Diseases", *Pediatr.*, 1993, 92:431–435). NEC was confirmed in 15 of the Control infants and only 1 of the Experimental group.

TABLE VI

Results of Clinical Study

|  | Control | Experimental |
|---|---|---|
| NEC* | 15 | 1 |
| no NEC | 70 | 32 |
| TOTAL | 85 | 33 |

*or suspected of NEC

Statistical analysis of this data, using Fisher's exact test (two tailed), shows that the number of infants confirmed with NEC in the Control treatment group(s) was significantly greater (P=0.039) than the number of infants in the Experimental treatment group having NEC.

EXAMPLE V

In this experiment, the inclusion of AA and DHA into parenteral (intravenous feedings) administration of nutrition, is evaluated. The parenteral solution can contain the various components known in the art with the AA and DHA being supplied in the form of a phospholipid, triglycerides or the methyl esters. The AA and DHA may be the sole active ingredients admixed with conventional parenteral vehicles and excipients or, more preferably, the AA and DHA is included a parenteral formula intended to supplement or supply the total nutritional support of the infant. Typical parenteral nutritional solutions contain levels of lipids resulting in about 2 g/kg/day. The level of AA and DHA in the lipid blend should result in the administration of from 10 to 25 mg/kg/d of AA and 5 to 15 mg/kg/d for DHA.

EXAMPLE VI

In this experiment, the egg lecithin of the experimental formula of Example II is replaced by soy lecithin at the approximately ten-fold higher levels than found in the control formula. Soy lecithin, like other phospnolipids derived from vegetable sources, contain no long-chain polyunsaturated acids; however, the polar nature of phospholipids and their ability to be readily incorporated into the intestinal mucosa may afford a protective effect on the intestinal lining, thereby producing results comparable to those of the experimental formula of Example II. Additionally, soy lecithin contains linoleic acid (18:2ω-6—a dietary essential fatty acid precurser to AA) and linolenic acid (18:3ω-3—a dietary essential fatty acid precurser DHA).

EXAMPLE VII

In this experiment, the use of phospholipids containing AA and DHA in infant formula is compared to triglycerides containing AA and DHA. The formula of Example II is compared to a similar infant formula wherein the egg phospholipid is replaced with a mixture of single cell microbial triglycerides containing comparable levels of AA and DHA.

Healthy full term infants are enrolled in a clinical evaluation to measure the blood serum levels of AA and DHA following enteral administration. It is expected that infants fed the phospholipid formula will achieve blood serum levels of AA and DHA more closely resembling those of breast fed infants than the control formula containing AA and DHA in triglyceride form. This experiment should demonstrate that phospholipids containing AA and DHA are a preferred form of administration over triglycerides containing AA and DHA. Thus, improved enteral formulas and methods for increasing AA and DHA blood serum levels are contemplated herein.

Modifications and alternative embodiments of the compositions and methods of the present invention will be apparent to those skilled in the art in view of the foregoing description. Accordingly, this description is to be construed as illustrative only and is for the purpose of teaching those of skill in the art the manner of carrying it out.

What is claimed is:

1. A process for the production of an infant formula containing egg phospholipids having improved organoleptic properties comprising the steps of:
   (a) forming a 2–15% by weight aqueous dispersion of egg phospholipids;
   (b) subjecting said dispersion to de-aeration;
   (c) combining said de-aerated dispersion with a mixture of protein, carbohydrates, vitamins and minerals, to form said infant formula; and
   (d) homogenizing said infant formula.

2. The process according to claim 1 wherein said aqueous dispersion is formed at ambient temperatures.

3. The process according to claim 1 wherein said aqueous dispersion is about 3 to about 6% by weight egg phospholipids.

4. A method of using an infant formula according to claim 1 to increase the levels of arachidonic acid and docosahexaenoic acid in an infant's blood serum, comprising administering said formula enterally to said infant.

5. A method of using an infant formula according to claim 4 wherein said egg phospholipid provides arachidonic acid in a concentration of from about 10 to about 31 mg per 100 kcals.

6. A method of using an infant formula according to claim 5 wherein said egg phospholipid provides docosahexaenoic acid in a concentration of from about 3 to about 16 mg per 100 kcals.

7. A method of using an infant formula according to claim 6 wherein said arachidonic acid and docosahexaenoic acid are present in a ratio of about 4:1 to about 2:1.

8. A process for the production of an enteral formula comprising egg phospholipids, said method comprising the steps of:
 (a) providing egg phosphatide essentially free of cholesterol;
 (b) dispersing said egg phosphatide at about at least 2 percent by weight in an aqueous phase to form a phospholipid dispersion prior to mixing said phospholipid with any other lipid component; and
 (c) combining said phospholipid dispersion with slurries of other components of said enteral formula.

9. The process according to claim 8 wherein said phospholipid dispersion comprises from about 2 to about 15% by weight of said egg phospholipids.

10. The process according to claim 9 wherein said phospholipid dispersion comprises adding said egg phosphatide to water at about 20 to about 50° C.

11. The process according to claim 8 wherein said phospholipid dispersion comprises from about 3 to about 6% by weight of said egg phospholipids.

12. The process according to claim 8 wherein said dispersing in aqueous phase comprises adding said egg phosphatide to water at less than about 50° C.

13. The process according to claim 8 wherein said dispersing in aqueous phase comprises adding said egg phosphatide to water at about 20 to about 50° C.

14. The process according to claim 8 wherein said phospholipid dispersion is subjected to de-aeration before combining said de-aerated phospholipid dispersion with said slurries of other components of said enteral formula.

15. A method of using an enteral formula according to claim 8 to increase the levels of w6 fatty acids and w3 fatty acids in human blood serum, comprising administering said formula enterally to said human.

16. The method of using an enteral formula according to claim 15 wherein said egg phospholipid provides w6 fatty acids in a concentration of from about 100 to about 425 mg per liter.

17. The method of using an enteral formula according to claim 16 wherein said egg phospholipid provides w3 fatty acids in a concentration of from about 40 to about 185 mg per liter.

18. The method of using an enteral formula according to claim 17 wherein said w6 fatty acids and said w3 fatty acids are present in a ratio of about 2:1 to about 3:1.

\* \* \* \* \*